(12) United States Patent
Karvir et al.

(10) Patent No.: US 12,125,563 B2
(45) Date of Patent: *Oct. 22, 2024

(54) SYSTEM AND METHOD FOR PREDICTING SUBJECT ENROLLMENT

(71) Applicant: MEDIDATA SOLUTIONS, INC., New York, NY (US)

(72) Inventors: Hrishikesh Karvir, Langhorne, PA (US); Fanyi Zhang, Jersey City, NJ (US); Jingshu Liu, Jersey City, NJ (US); Michael Elashoff, Hillsborough, CA (US); Christopher Bound, Perkasie, PA (US)

(73) Assignee: MEDIDATA SOLUTIONS, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/937,899

(22) Filed: Oct. 4, 2022

(65) Prior Publication Data

US 2023/0026758 A1 Jan. 26, 2023

Related U.S. Application Data

(63) Continuation of application No. 15/980,532, filed on May 15, 2018, now Pat. No. 11,494,680.

(51) Int. Cl.
*G16H 10/20* (2018.01)
*G16H 50/30* (2018.01)
(Continued)

(52) U.S. Cl.
CPC ............ *G16H 10/20* (2018.01); *G16H 50/30* (2018.01); *G16H 50/50* (2018.01); *G16H 50/70* (2018.01);
(Continued)

(58) Field of Classification Search
CPC .......... G06N 7/01; G06N 20/00; G06N 3/045; G16H 10/20; G16H 50/30; G16H 50/50; G16H 50/70; G16H 80/00
See application file for complete search history.

(56) References Cited

U.S. PATENT DOCUMENTS 5,649,065 A * 7/1997 Lo .......................... G06N 3/044
706/41
7,085,690 B2 8/2006 Sale
(Continued)

FOREIGN PATENT DOCUMENTS

JP 2020-535514 A 12/2020

OTHER PUBLICATIONS

Tomer et al., "Personalized Schedules for Surveillance of Low Risk Prostate Cancer Patients" Nov. 1, 2017, arXiv: 1711.00285v1, pp. 1-16. (Year: 2017).*

(Continued)

*Primary Examiner* — Vincent Gonzales
*Assistant Examiner* — Chase P. Hinckley
(74) *Attorney, Agent, or Firm* — STEPTOE LLP; Carl B. Wischhusen

(57) ABSTRACT

A system for predicting subject enrollment for a study includes a time-to-first-enrollment (TTFE) model and a first-enrollment-to-last-enrollment (FELE) model for each site in the study. The TTFE model includes a Gaussian distribution with a generalized linear mixed effects model solved with maximum likelihood point estimation or with Bayesian regression, and the FELE model includes a negative binomial distribution with a generalized linear mixed effects model solved with maximum likelihood point estimation or with Bayesian regression estimation.

11 Claims, 9 Drawing Sheets

(51) Int. Cl.
*G16H 50/50* (2018.01)
*G16H 50/70* (2018.01)
*G06N 3/045* (2023.01)
*G06N 7/01* (2023.01)
*G06N 20/00* (2019.01)

(52) U.S. Cl.
CPC ............... *G06N 3/045* (2023.01); *G06N 7/01* (2023.01); *G06N 20/00* (2019.01)

(56) References Cited

U.S. PATENT DOCUMENTS

| | | | |
|---|---|---|---|
| 8,706,537 | B1 | 4/2014 | Young et al. |
| 10,311,442 | B1* | 6/2019 | Lancaster ............... G16H 10/00 |
| 10,311,534 | B2* | 6/2019 | Schultz ............... G06Q 30/0205 |
| 10,395,198 | B2 | 8/2019 | Blomberg et al. |
| 10,515,099 | B2 | 12/2019 | Dietlin et al. |
| 10,740,437 | B1* | 8/2020 | Shannon ............... G16H 10/60 |
| 11,107,559 | B1* | 8/2021 | Wynden ............... G16H 10/40 |
| 2006/0184493 | A1 | 8/2006 | Shiffman et al. |
| 2006/0282244 | A1 | 12/2006 | Chotai et al. |
| 2009/0292554 | A1* | 11/2009 | Schultz ............... G16H 10/00 705/7.34 |
| 2009/0313048 | A1 | 12/2009 | Kahn et al. |
| 2011/0238317 | A1 | 9/2011 | Freedman |
| 2011/0238438 | A1* | 9/2011 | Houriet, Jr. ............. G16H 10/20 705/2 |
| 2011/0264609 | A1* | 10/2011 | Liu ............... G06N 20/00 706/12 |
| 2013/0346094 | A1* | 12/2013 | Goodgame ............ G16H 10/60 705/2 |
| 2014/0278469 | A1* | 9/2014 | Secci ............... G16H 10/20 705/2 |
| 2014/0324553 | A1* | 10/2014 | Rosenberg ............. G16H 10/20 705/7.41 |
| 2015/0074133 | A1 | 3/2015 | de Vries et al. |
| 2015/0120725 | A1 | 4/2015 | de Vries et al. |
| 2015/0286802 | A1* | 10/2015 | Kansara ............... G16H 10/20 705/3 |
| 2016/0042155 | A1* | 2/2016 | Li ............... G16H 50/20 705/2 |
| 2016/0180276 | A1* | 6/2016 | Bound ............... G16H 10/20 705/2 |
| 2016/0270659 | A1* | 9/2016 | Gandhi ............... G16B 50/30 |
| 2016/0300040 | A1* | 10/2016 | Dietlin ............... G16H 10/20 |
| 2017/0220773 | A1 | 8/2017 | Janevski et al. |
| 2017/0270279 | A1* | 9/2017 | Li ............... G16H 10/20 |
| 2018/0046780 | A1* | 2/2018 | Graiver ............... G06F 40/44 |
| 2019/0096510 | A1* | 3/2019 | Tourtellote ............ G06F 16/335 |
| 2019/0206521 | A1* | 7/2019 | Walpole ............... G16H 40/20 |
| 2019/0304575 | A1* | 10/2019 | Beltre ............... G16H 40/20 |
| 2020/0168304 | A1* | 5/2020 | Manasco ............... G16H 10/20 |
| 2020/0350041 | A1 | 11/2020 | Li |

OTHER PUBLICATIONS

Soleimani et al., "Treatment-Response Models for Counterfactual Reasoning with Continuous-time, Continuous-valued Interventions" Nov. 5, 2017, arXiv: 1704.02038v2, pp. 1-11. (Year: 2017).*
Lim et Van der Schaar, "Disease-Atlas: Navigating Disease Trajectories using Deep Learning" Apr. 20, 2018, arXiv: 1803.10254v2, pp. 1-24. (Year: 2018).*
Bustos et Pertusa, "Learning Eligibility in Cancer Clinical Trials using Deep Neural Networks" Mar. 23, 2018, arXiv: 1803.08312v2, pp. 1-26. (Year: 2018).*
Zhang, N., "Simulation Study on Local Influence Diagnosis for Poisson Mixed-Effect Linear Model" May 8, 2018, arXiv: 1805.02898v1, pp. 1-13. (Year: 2018).*
Li et Redden, "Comparing denominator degrees of freedom approximation for the generalized linear mixed model in analyzing binary outcome in small sample cluster-randomized trials" 2015, pp. 1-12. (Year: 2015).*
Comfort, "Improving Clinical Trial Enrollment Forecasts Using SORM", Applied Clinical Trials, vol. 22, Issue 5, May 1, 2013, 19 pages. Retrieved Dec. 22, 2021 from https://www.appliedclinicaltrialsonline.com.
Friedman, "Stochastic gradient boosting", Computational Statistics & Data Analysis 38, 2002, pp. 367-378.
Heitjan et al. "Real-time prediction of clinical trial enrollment and event counts: A review", Contemporary Clinical Trials 45, 2015, pp. 26-33.
Jiang et al. "Modeling and validating Bayesian accrual models on clinical data and simulations using adaptive priors", Statist. Med. 34, 2015, pp. 613-629.
Karth, "6 Common Probability Distributions every data science professional should know", Web article posted at Analytics Vidhya on Sep. 18, 2017, 14 pages. Retrieved Dec. 22, 2021 from https://www.analyticsvidhya.com/blog/2017/09/6-probability-distributions-data-science.
McCulloch, "Maximum Likelihood Algorithms for Generalized Linear Mixed Models", Biometrics Unit and Statistics Center Cornell University, Nov. 1995, 24 pages. Retrieved Dec. 22, 2021 from https://ecommons.cornell.edu.
Williams, "Maximum Likelihood vs. Bayesian Parameter Estimation. Slide deck prepared for course lecture", CSG 220, Spring 2007, 11 pages. Retrieved Dec. 7, 2021 from https://www.ccs.neu.edu/home/rjw/csg220/lectures/MLE-vs-Bayes.pdf.
Zhang et al. "Modeling and prediction of subject accrual and event times in clinical trials: a systematic review", Clin. Trials 9, 2012, pp. 681-688.
Encyclopedia of Statistical Sciences, edited by Samuel Kotz et al., published by John Wiley & Sons, 1985. vol. 2, pp. 193-204; vol. 2, pp. 389-397; vol. 3, pp. 137-141; vol. 5, pp. 128-133.
National Research Council (US) Panel on Handling Missing Data in Clinical Trials. The Prevention and Treatment of Missing Data in Clinical Trials, Appendix A Clinical Trials: Overview and Terminology. Washington (DC): National Academies Press (US), 2010, 10 pages. Retrieved Dec. 22, 2021 from https://www.ncbi.nlm.nih.gov/books/NBK209903/?report=printable.

* cited by examiner

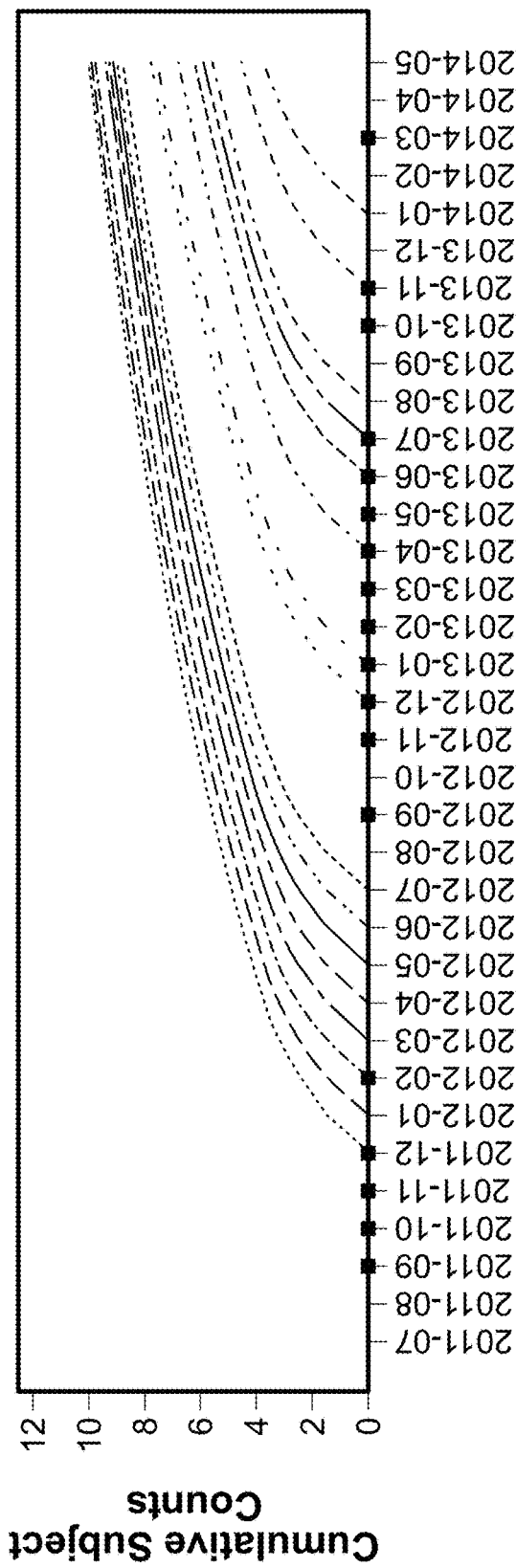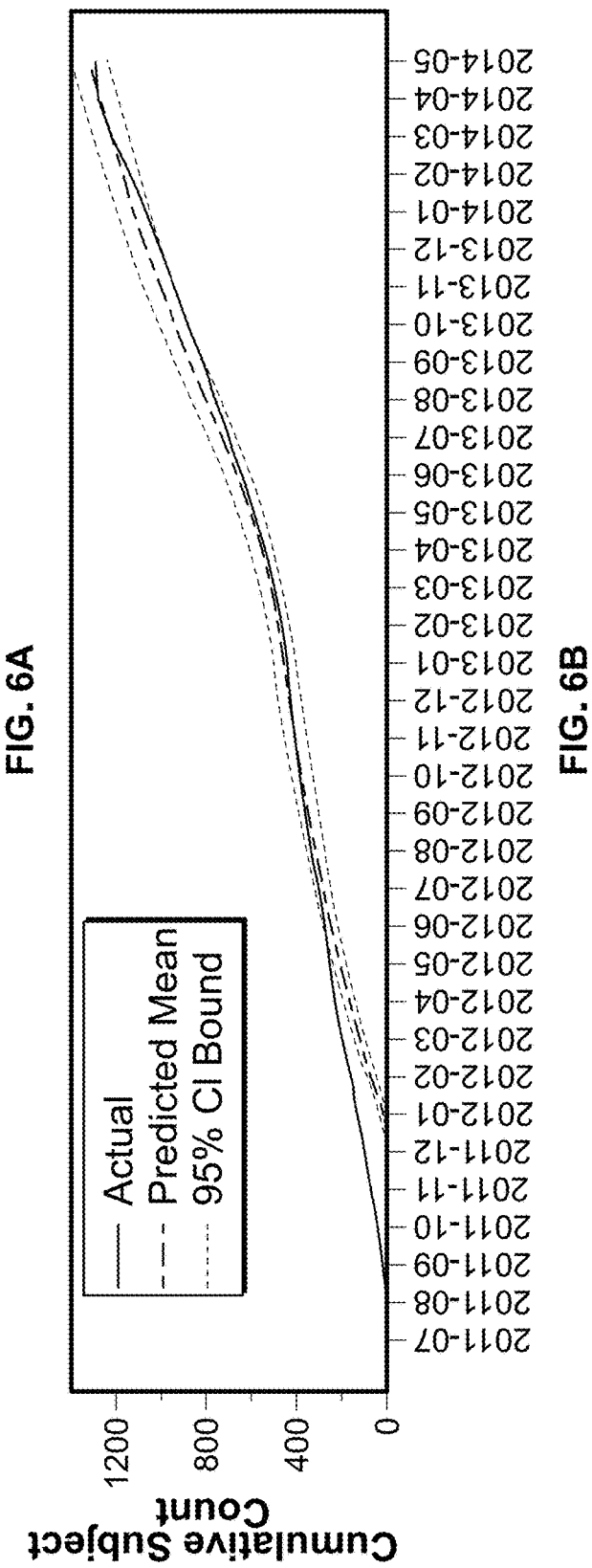

SYSTEM AND METHOD FOR PREDICTING SUBJECT ENROLLMENT

CROSS-REFERENCE TO RELATED APPLICATION(S)

This application is continuation of U.S. patent application Ser. No. 15/980,532, filed May 15, 2018, the disclosure of which is hereby incorporated by reference in its entirety.

BACKGROUND

Estimating subject recruitment in a large scale, multi-center randomized clinical trial (or clinical study) is challenging. In many cases a majority of clinical trial sites fail to meet enrollment requirements. Accurate enrollment prediction allows trial sponsors and contract research organizations (CROs) to better plan the timing and execution of a clinical trial.

BRIEF DESCRIPTION OF THE DRAWINGS

FIG. 6A is a graph of site-level predictions generated for one particular study, according to an embodiment of the present invention;

FIG. 6B is a graph of a study-level cumulative subject estimate from the sites in FIG. 6A, according to an embodiment of the present invention.

Figure 1:
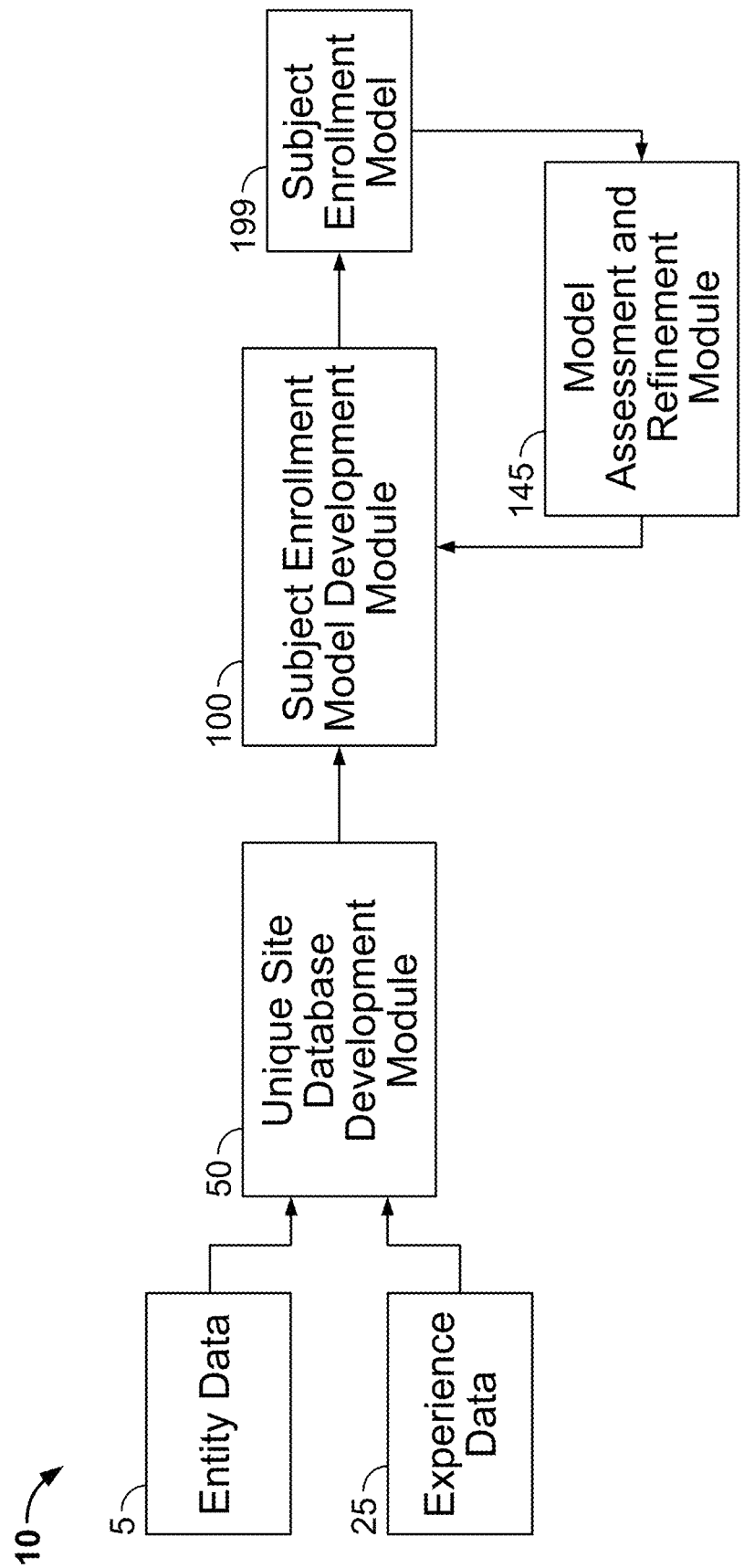
FIG. 1 is a system diagram illustrating development of a unique site database and a model for predicting subject enrollment, according to an embodiment of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

The inventors have developed a system and method to predict subject enrollment in a clinical trial using a standardized database of sites and a combination of sub-models for different time periods of enrollment. This system can provide researchers and/or sponsors the ability to predict an individual site's performance for a given study, so as to facilitate site selection based on predicted performance. Then, for a collection of sites, the system can generate study-level predictions for time-to-target enrollment and also estimate the number of subjects for a given period. As the study progresses, the system can periodically revise predictions based on the observed performance from the recruited sites and changes in the study/site environment, to provide improved estimates on recruitment. Such revisions may allow researchers and/or sponsors to prepare rescue sites if there is an expected enrollment slowdown. Contributing to the success of the system and method is a way to standardize clinical trial sites to identify specific sites' past behavior and recognize the relationship between certain metrics and enrollment prediction to leverage metrics from other sites.

Advantages over prior approaches to the problem of predicting subject enrollment include the ability to generate a standardized database of sites, to keep track of the relevant information important for predicting subject enrollment, and to use information from other sites having some common attribute (e.g., phase, therapeutic area, indication, etc.) to augment deficiencies in information for any specific site. The system understands that different attributes have different effects on the ability to predict subject enrollment and exploits these differences using hierarchical statistical models.

Reference is now made to FIG. 1, which is a diagram of a system 10 illustrating development of the standardized or unique site database and a model for predicting subject enrollment. The two main parts are unique site database development module 50 and subject enrollment model development module 100. Entity data 5 and experience data 25 are input to unique site database development module 50 to generate a unique site database. That database is used in subject enrollment model development module 100 to generate subject enrollment model 199, which is assessed and refined using model assessment and refinement module 145.

Figure 2A:
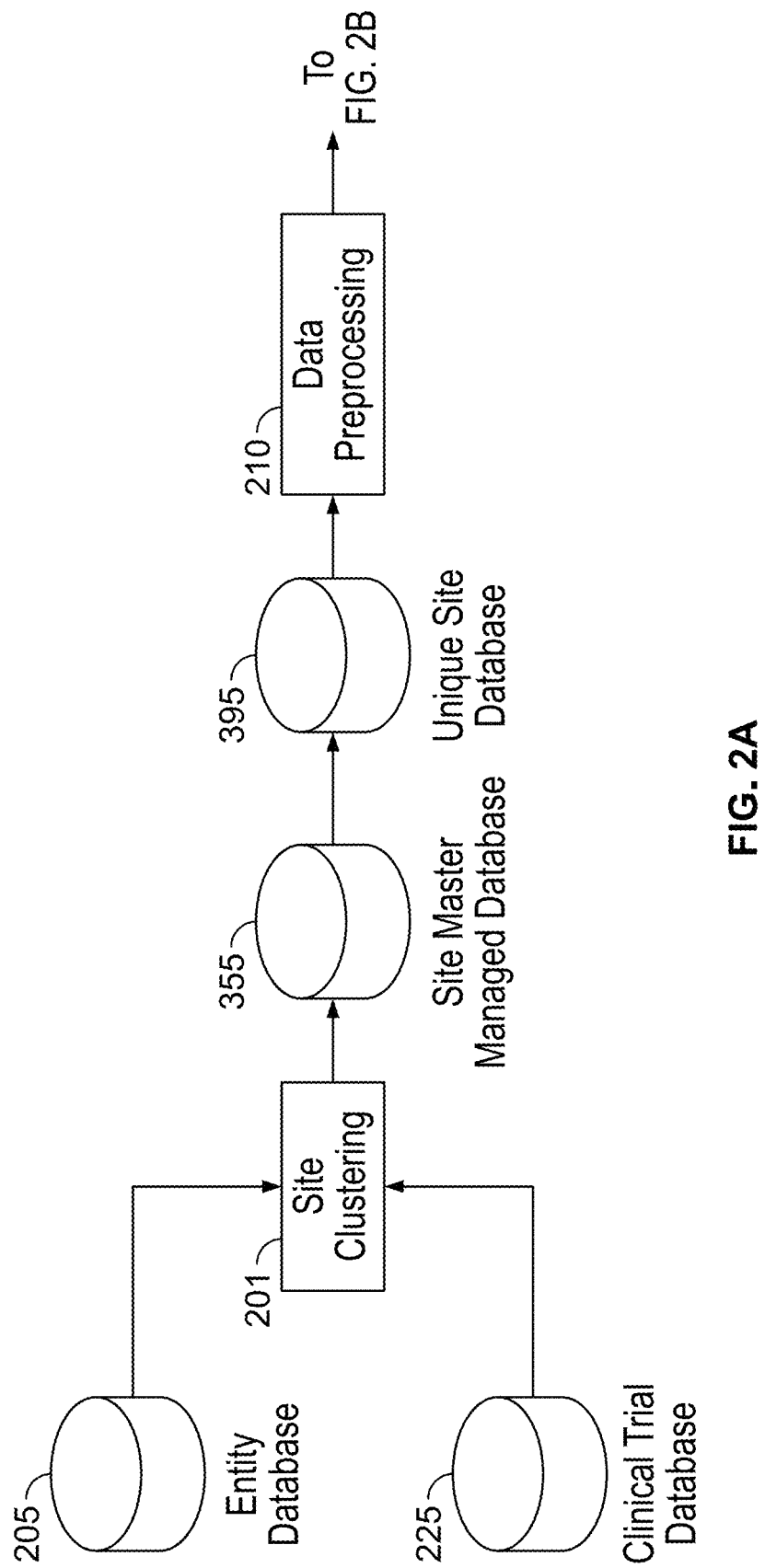
FIGS. 2A and 2B make up a diagram showing the two parts of FIG. 1 in more detail, according to an embodiment of the present invention.
Figure 2B:
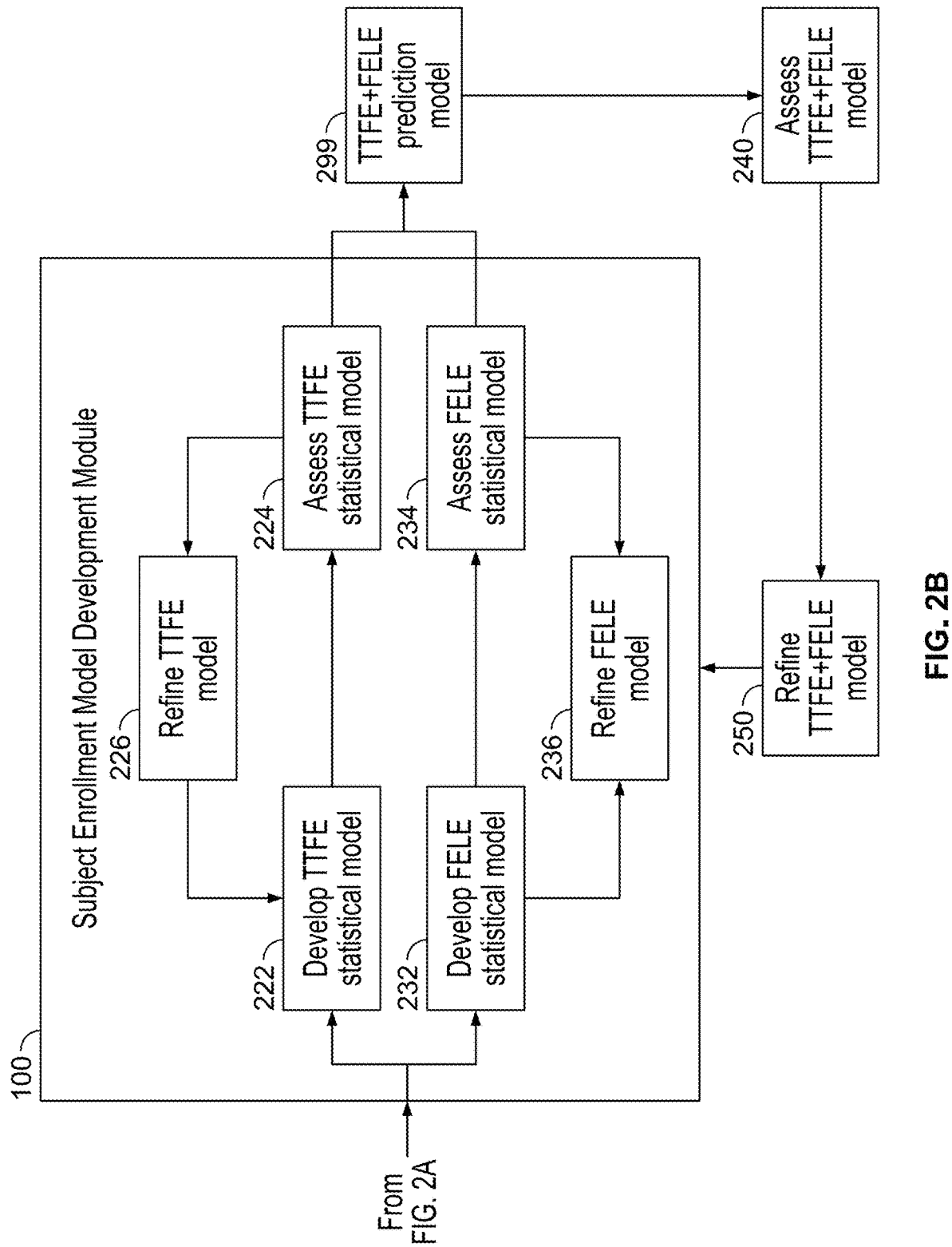

Reference is now made to FIGS. 2A and 2B, which show the two parts of system 10 in more detail. In FIG. 2A, entity data 5 may be collected in entity database 205, which includes lists of entities, including entities and sites that may participate in a clinical trial. Entity database 205 may comprise proprietary and public information about a wide range of entities, such as corporations and other business associations. Examples of proprietary databases are those developed by NAICS Association (North American Industry Classification System), Hoover's, Orbis, Dun & Bradstreet, and Bloomberg, but other proprietary databases exist. Other information in entity database 205 (or even much of the same information) may be available from public databases, such as those found on the Internet. Experience data 25 may be collected in clinical trial database 225, which may include any type of clinical and operational data collected during one or more clinical trials. Such data may be manually entered and/or may be electronically captured using, for example, an electronic data capture (EDC) program, a clinical trial management system (CTMS), or other data collection systems.

The information in entity database 205 and clinical trial database 225 may be input to site clustering module 201 to generate site master managed database 355, as will be described in more detail in FIG. 3 below. These databases may be used to generate unique site database 395 (a database of unique healthcare sites), which is a centralized location for all operational metrics collected in clinical trials, including study-level characteristic metrics such as phase, therapeutic area, study indication group, study indication, etc., site-level operational metrics such as site activation date, data query rate, etc., and subject-level disposition statuses and dates. This database contains information from thousands of clinical trials and three to four times that number of unique clinical sites standardized from site master data managed database 355.

Figure 3:
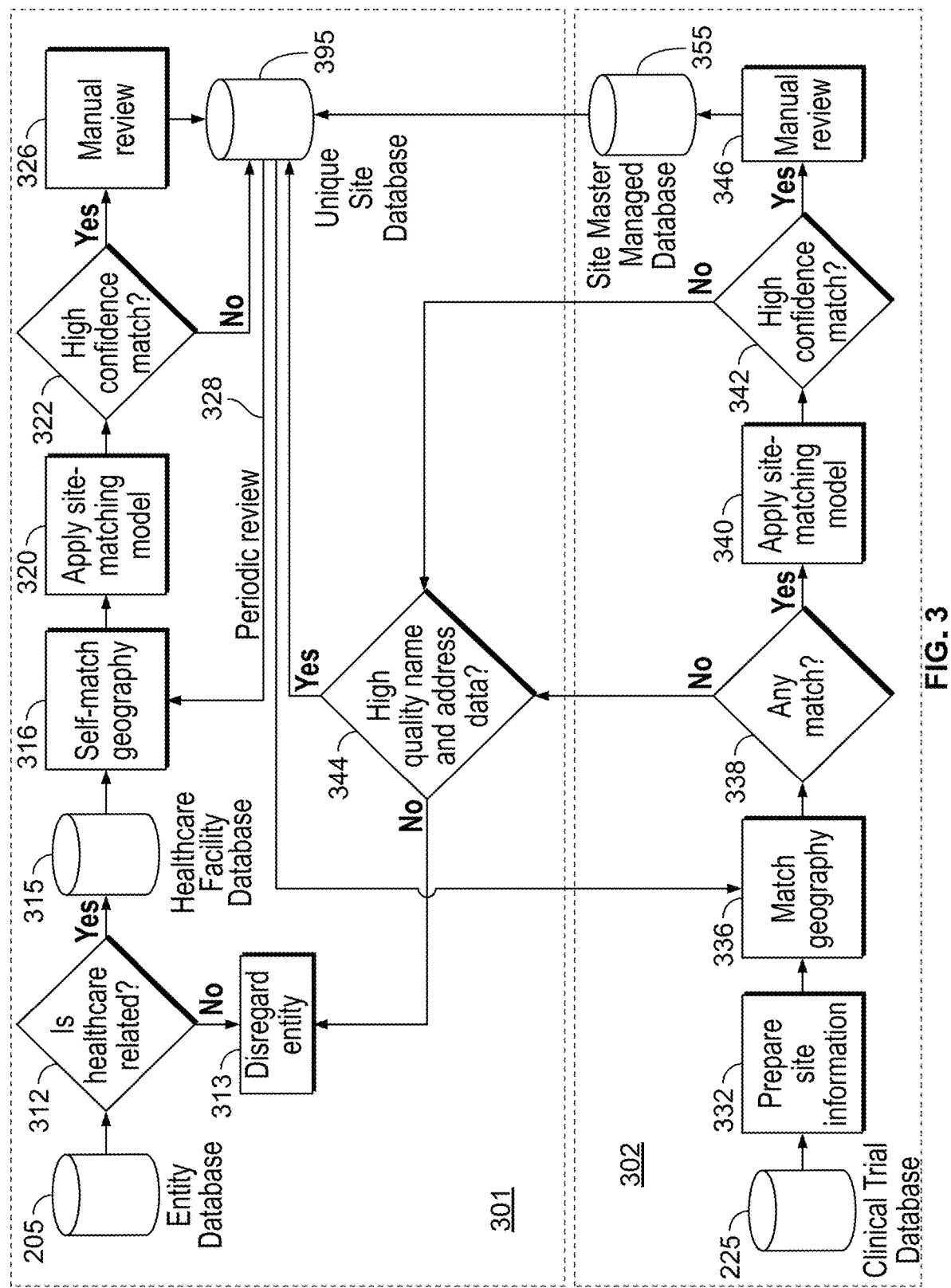
FIG. 3 is a diagram showing the details of how the unique site database from FIG. 2A may be generated, according to an embodiment of the invention.

FIG. 3 shows the details of how unique site database 395 may be generated, according to an embodiment of the invention. There are two main modules, 301 and 302. Module 301 generates part of unique site database 395 based on entity database 205; module 302 generates site master managed database 355 based on clinical trial database 225; site master managed database 355 is then integrated with unique site database 395.

In module 301, the information about each entity is queried in operation 312 to determine whether it is healthcare related. The information entity database 205 includes about an entity may be corporate name, alternative names, address, phone, officers, industry categorization, etc. Operation 312 may look at the industry categorization and the corporate and alternative names in the database entry to determine whether the entity has some relation to healthcare, for example, a hospital, a clinic, a doctor, etc. If so, then that entity is included in an intermediate healthcare facility database 315. If not, then that entity is disregarded in operation 313. Then, the process attempts to find duplicates in healthcare facility database 315. In operation 316, each site in healthcare facility database 315 is compared to other entities in the database by geography, such as a country, state, and/or postal code. In operation 320, a site-matching model comprising a gradient boosting method (GBM) classification model may be used that calculates a matching probability for each healthcare facility pair, by evaluating the similarity of site attributes such as name, alias, address, phone number, etc. Healthcare facility database 315 may include aliases that it has learned, which are names that the entity may otherwise be known as, for example, "Sloan Kettering" and "Sloan Kettering Memorial Hospital." The healthcare facility pair with the highest matching probability is considered to be a "match." In operation 322, the output of the GBM model is evaluated, and if the output is greater than or equal to a certain threshold (or confidence level), then it is called a "high-confidence match." High confidence matches are then manually reviewed in operation 326 to group matched pairs (duplicates) into a unique entity, which is assigned a unique healthcare facility ID in unique site database 395. If a site does not have a high-confidence match, then the site is directly added to unique site database 395. Operation 328 periodically reviews unique site database 395 for duplications as new site attributes and alias information accumulate, e.g., when there are incremental changes in healthcare facility database 315 (e.g., more entity data have been received), if more unique sites are added via operation 344 (described below), or more site-alias information is added via site master managed database 355 (described below). This is done to determine whether the remaining and/or added sites in healthcare facility database 315 or unique site database 395 should be grouped together.

Moving to module 302, the information for each site from clinical trial database 225 may be prepared (or cleaned) in operation 332 using a series of text processing and normalization steps, such as standardizing state names, removing text from phone numbers, etc. In operation 336, each site in clinical trial database 225 is compared to entities in unique site database 395 by geography, such as a country, state, and/or postal code, as in operation 316. If no match is made in operation 338, then it is assumed that the site is either new or with such poor data quality that it cannot be identified. If that site includes high quality name and address data as determined in operation 344, then the site may be added directly to unique site database 395, otherwise the entity is disregarded in operation 313. "High quality" may mean that both name and address exist and are recognizable, e.g., "Sloan Kettering Memorial Hospital" would be a high-quality name, but "SKM" would not be. Similarly, "Cleveland Clinic" without an address is not high quality, if it cannot be determined whether the site is in Ohio or Florida.

If a match is made in operation 338, then operation 340 may use the GBM site-matching classification model to calculate a matching probability for each clinical trial site-unique site database pair by evaluating the similarity of site attributes such as name, alias, address, phone number, etc. Unique site database 395 may include aliases that have been learned, as was described in operation 320. The site in database 395 with the highest matching probability is considered to be the "match," and its site ID is assigned to the site from clinical trial database 225. In operation 342, the output of the GBM model is evaluated and if it is greater than a certain threshold (or confidence level), then it is called a "high-confidence match." High confidence matches are then manually reviewed in operation 346 to assign the ID in unique site database 395 to sites in site master data managed database 355, which maps sites to studies. Database 355 may include duplicates, because one site may have participated in multiple studies. Less than high-confidence matches may be evaluated in operation 344 to determine if that site includes high quality name and/or address data as discussed above and, if so, then the site may be added directly to unique site database 395. The information in site master managed database 355 may then be integrated into unique site database 395, including adding alias information to the record for the unique facility ID.

Besides the operations shown in FIG. 3, other operations or series of operations are contemplated to generate site master managed database and the unique site database. For example, healthcare facility database 315 need not be fully generated in order to perform operation 316 and those that follow. The site preparation described in operation 332 may also be used for entities in entity database 205. Matching algorithms other than GBM may be used. Moreover, the actual order of the operations in the flowchart in FIG. 3 is not intended to be limiting, and the operations may be performed in any practical order.

Returning to FIG. 2A, once unique site database 395 is generated, data preprocessing 210 may occur. In this operation, the standardized data are preprocessed to remove outliers, and the data are restructured to represent daily, weekly, monthly, quarterly, semi-annual, or annual recruitment per study-site. Monthly subject recruitment per study-site was initially used to develop the prediction model, and quarterly predictions may be used. The following factors were used as initial predictors to build the statistical model, grouped in three broad categories: (1) study-level predictors, (2) site-level predictors, and (3) subject-level predictors.

Study-level predictors include (a) phase, (b) therapeutic area, (c) indication group, (d) indication, (e) sponsor name, (f) whether the study accepts healthy volunteers, and (g) study complexity. Site-level predictors include (a) site history (captured through the unique site master managed database site ID), (b) site burden (number of concurrent studies from different sponsors at a site at any given time), (c) enrollment duration (daily, weekly, monthly, quarterly, or yearly increments), (d) site location, and (e) site activation schedule. Subject-level predictors include (a) disease prevalence, (b) patient availability, and (c) population density.

Figure 4:
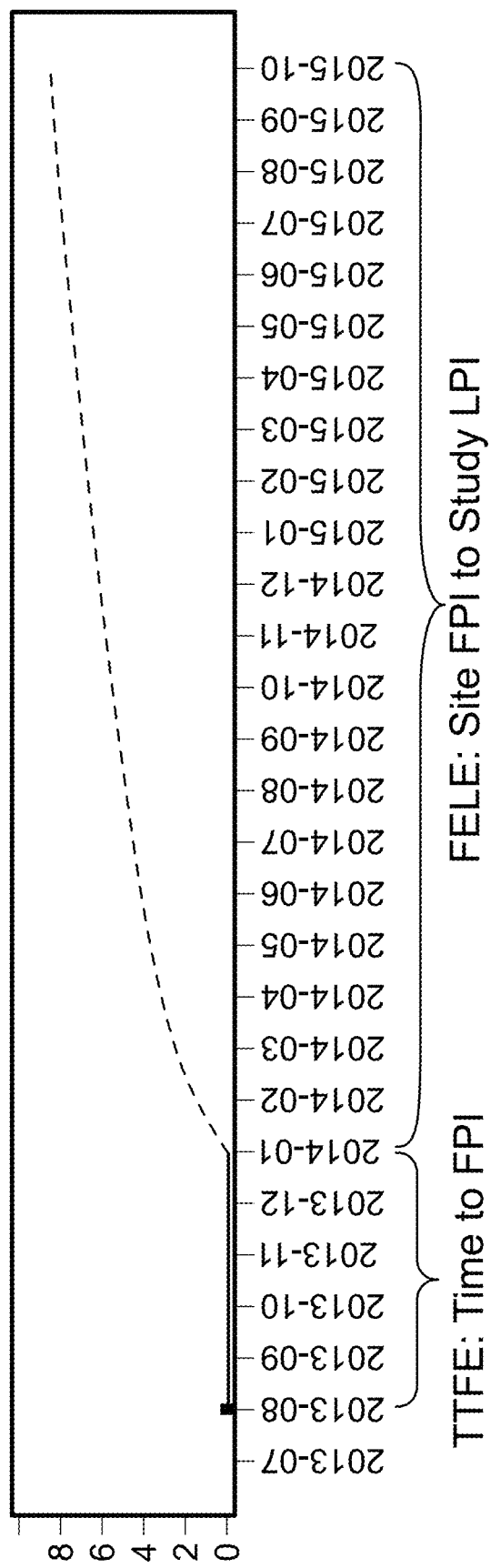
FIG. 4 is a graph showing two parts of an enrollment timeline to be modeled, according to an embodiment of the present invention.

The output of data preprocessing module 210 in FIG. 2A is input to subject enrollment model development module 100 in FIG. 2B. The inventors determined that predicting subject enrollment can be modeled by breaking up the enrollment timeline into at least two parts, and applying different models to each part, as shown in FIG. 4. The first part is "time to first enrollment" or TTFE; the second part is "first enrollment to last enrollment" or FELE. The TTFE model predicts the time from site activation (SA) to first patient in (FPI) for each site; the FELE model predicts the monthly subject count from FPI for a site to last patient in (LPI) for the study.

The general process for developing the subject enrollment model is shown in FIG. 2B. In operation 222, the TTFE statistical model is developed, then it is assessed in operation 224, and then the model is refined in operation 226. Similarly, in operation 232, the FELE statistical model is developed, then it is assessed in operation 234, and then that model is refined in operation 236. The combination TTFE+FELE model 299 is generated, and is subject to assessment in operation 240 and refinement in operation 250. Refinements in 226, 236, and 250 include determining which probability distribution, Poisson or negative binomial, is suitable for the outcome variable; determining whether to consider fixed, random, or mixed effects; determining which factors are predictive in each model; determining what model structure provides a generalizable result, while also providing the best performance (high correlation, low mean absolute error (MAE); and determining which model structure provides the highest performance.

To develop the models (blocks 222 and 232), the data were randomly split into training and testing sets by study. In one embodiment, there were 2300 studies and 11,000 unique sites in the training set, and over 1000 studies and 7000 unique sites in the testing set. A subset (~20%) of sites in the testing data was not part of the training data.

The blocks shown in FIGS. 1, 2A, 2B, and 3 are examples of modules that may comprise system 10 and do not limit the blocks or modules that may be part of or connected to or associated with these modules. The blocks in FIGS. 1, 2A, 2B, and 3 may be implemented in software or hardware or a combination of the two, and may include memory for storing software instructions.

Figure 5:
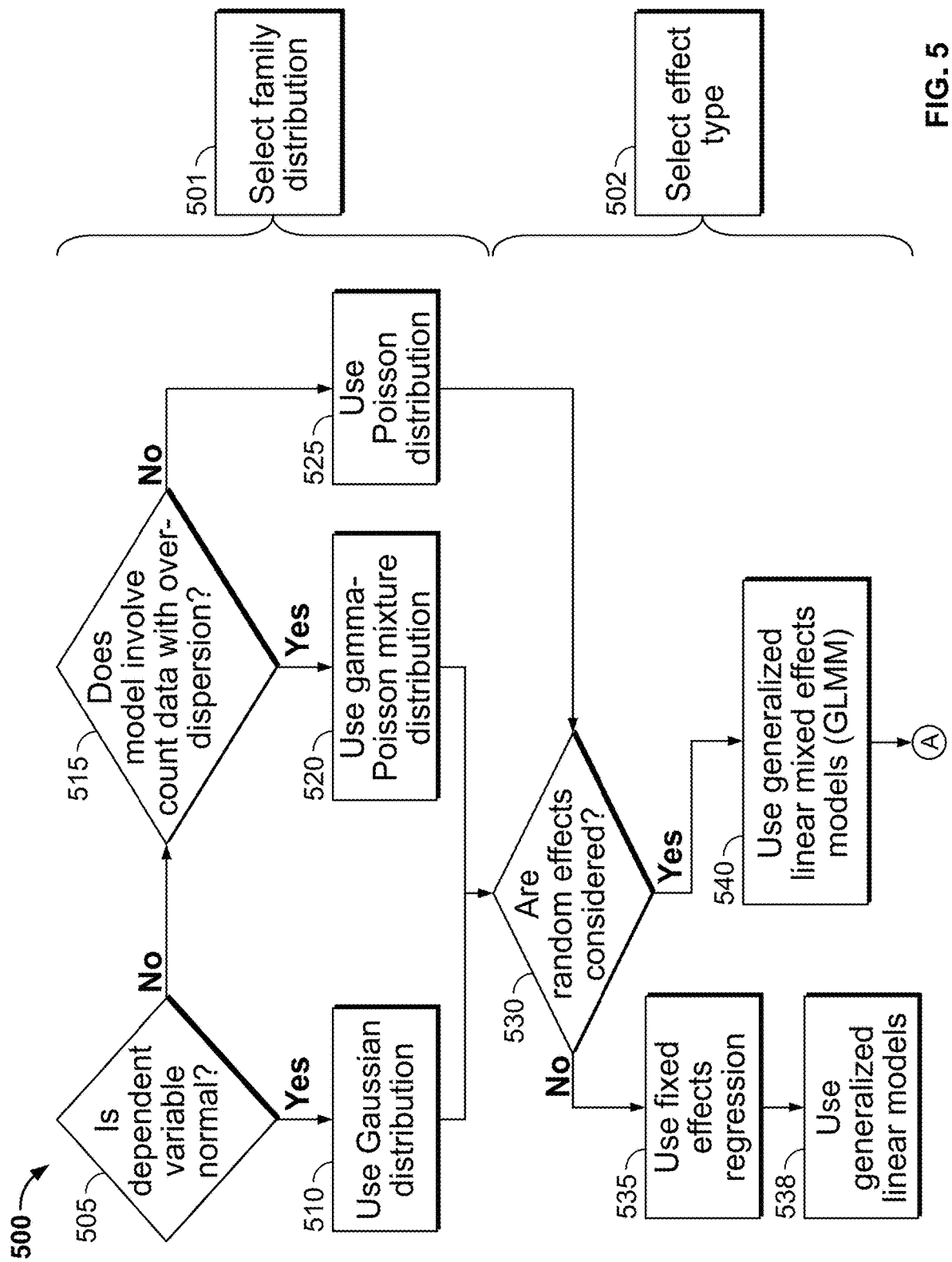
FIG. 5 is a flowchart showing the process for building each prediction model using the training set data, according to embodiments of the present invention.
Figure 5:
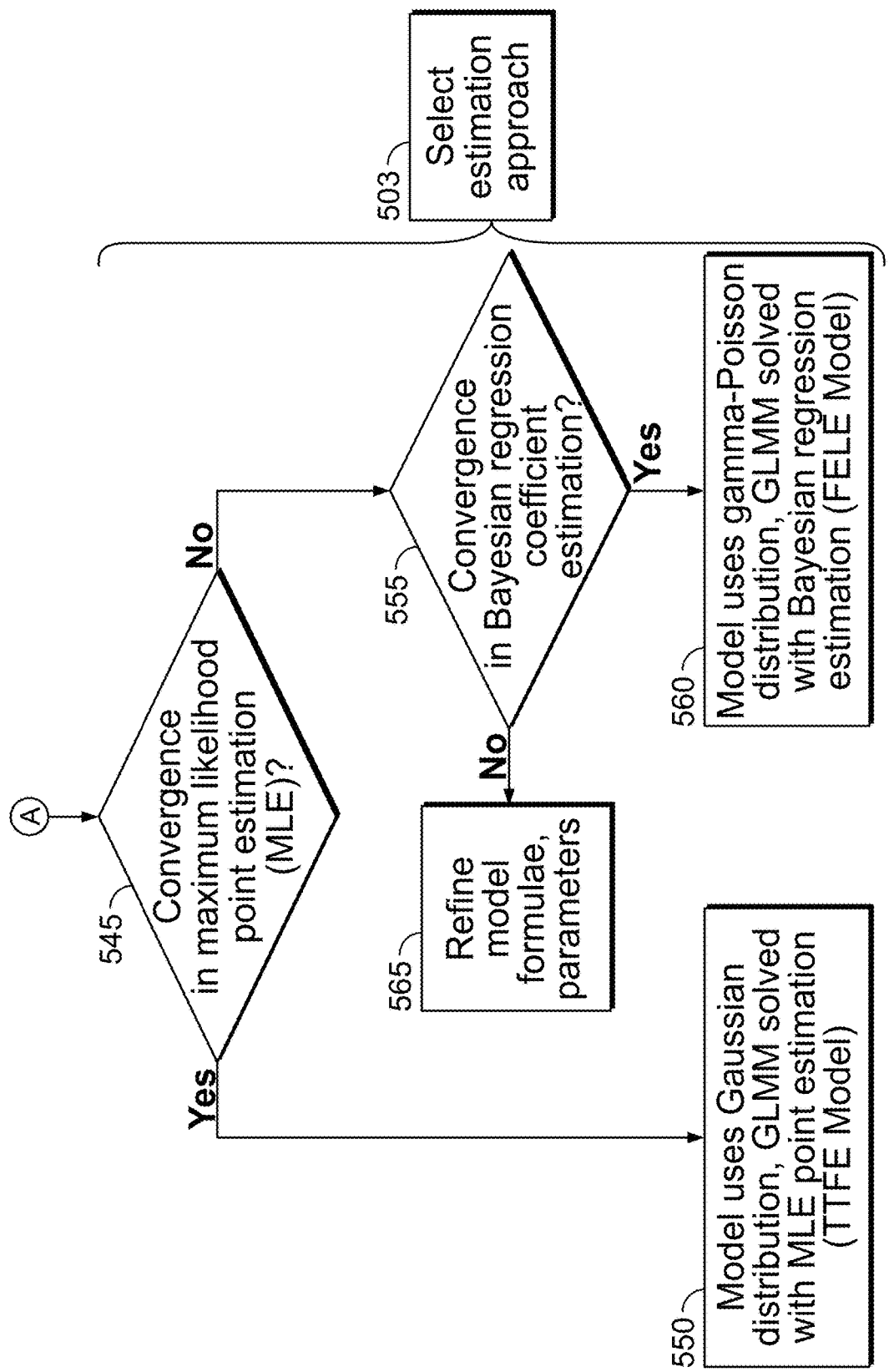

FIG. 5 is a flowchart showing the process for building each prediction model using the training set data. There are three main sections: section 501—selecting or identifying the family of the dependent variable distribution, section 502—selecting the effect type and the variables considered for each effect, and section 503—selecting the estimation approach (or optimization algorithm).

The possible distribution family is Gaussian, Poisson, or gamma-Poisson, a form of a negative binomial distribution in the context of this specification.

The possibilities for the effect type are fixed (global) effects, random (grouping) effects, and mixed effects (when a model includes both fixed and random effects). Fixed effects and random effects are typically defined in the context of groups, which in this case are defined at the study level, with therapeutic area (TA) at the top, and indication group and indication acting as subgroups within TA. The site ID may also act as a grouping factor to capture each site's history from various studies conducted at a given site. Fixed effects are constant across different groups/subgroups, whereas random effects allow for variation across groups/subgroups. For example, in one embodiment, the effect of enrollment duration is considered constant across different TAs, indication groups and indications, and sites, so it forms a fixed effect. Conversely, because each site's average enrollment performance and average enrollment performance across different TAs may be considered to be different, site ID and TA are considered to be random effects variables.

The possible optimization algorithm or estimation approach includes maximum likelihood point estimation (MLE) and Bayesian estimation.

Flowchart 500 operates as follows. Section 501 of the flowchart selects the family distribution of the outcome (dependent) variables being predicted in the context of this problem. Examples of dependent variables here are time taken by a site to enroll the first patient in a study (TTFE model) and the number of patients enrolled by a site in a given month for a study (FELE model). In operation 505, if the dependent variable is continuous and uses a normal distribution, or is transformable to a normal distribution, then the family distribution is Gaussian, as shown in operation 510. If the dependent variable is discrete, using count data, then operation 515 asks whether the model involves overdispersion. Overdispersion occurs when the underlying process generating the outcome variable has too much variability and needs an extra parameter to account for it. In other words, overdispersion means the data distribution has a heavy tail, and a standard Poisson distribution will not fit well with such data. If there is overdispersion, then the family distribution is a gamma-Poisson mixture, as shown in operation 520. If the model involves count data, but there is no overdispersion, then as shown in operation 525 the family distribution is Poisson, which requires fewer parameter estimates.

Once the family distribution is determined, section 502 selects the effect type. Operation 530 asks whether random (grouping) effects (including mixed (fixed and random) effects) are observed and need to be accounted for. If only fixed effects are considered, then operation 535 determines the effect type to be fixed effects regression, and a generalized linear model (GLM) may be used in operation 538. If random effects or mixed effects are observed, then operation 540 determines that the model is a generalized linear mixed effects model (GLMM). Mixed effects models are also called "hierarchical models," and a GLMM can capitalize on the grouping and hierarchy in the data to provide robust estimates for parameters based on strength of the evidence and group size.

Once the effect type is determined, section 503 selects the estimation approach. Operation 545 asks whether there is convergence using maximum likelihood point estimation (MLE). If so, then the model uses the Gaussian distribution, generalized linear mixed effects model solved with MLE point estimation, as shown by block 550. The inventors determined that this is a proper model for the TTFE model.

If there is no convergence using maximum likelihood estimation in operation 545, then operation 555 asks whether there is convergence using Bayesian regression coefficient estimation. If there is convergence with this type of regression, then the model uses the gamma-Poisson distribution, generalized linear mixed effects model solved with Bayesian regression estimation, as shown by block 560. The inventors determined that this is a proper model for the FELE model. However, had there not been convergence in operation 555, the model formulae and parameters would be refined in operation 565, as was described above with respect to blocks 226, 236, and 250.

Besides the operations shown in FIG. 5, other operations or series of operations are contemplated to generate the TTFE and FELE models. Although maximum likelihood point estimation was identified to be used for the TTFE model, that model may instead use Bayesian regression estimation. Similarly, although Bayesian regression estimation was identified to be used for the FELE model, that model may instead use maximum likelihood point estimation in certain cases. Moreover, the actual order of the operations in the flowchart in FIG. 5 is not intended to be limiting, and the operations may be performed in any practical order.

Because mixed effects regression is used for both the TTFE and FELE models, a subset of the study-level predictors, site-level predictors, and subject-level predictors (also called variables) listed above were considered as fixed effects (FE) variables, while the remaining were considered as random effects (RE) variables according to the following list:

FE variables: Site activation schedule, site burden, enrollment duration, study complexity, population density, and disease prevalence;

RE variables: Phase, therapeutic area, indication group, indication, site ID (i.e., identity of the clinical trial site), site location, and investigator.

A model formula can be generally expressed as follows, where $$\text{Outcome} = \text{Intercept} + FE1 + FE2 + \ldots + (FE1 + FE2 + \ldots | RE1/RE2 \ldots) + (FE1 + FE2 + \ldots \| RE1/RE2 \ldots)$$

Here, FE1, FE2, . . . indicate the different fixed effects variables, RE1, RE2, . . . indicate the different random effects variables, RE1/RE2 indicates RE2 is a variable nested under RE1 (for example, indication is nested under indication group), "|" indicates correlated random intercept and slope, and "||" indicates uncorrelated random intercept and slope. The use of random effects allows estimation of group-level effects (e.g., enrollment performance within a given indication, or within a given site) to let the model adjust for trends within a group. The nesting structure allows the model to regress to the mean of the higher group in a hierarchy when samples within a given subgroup are not sufficient (for example, if a given indication has less than 5 samples, but the indication group (which is composed of several related indications) has more than 100 samples, the coefficient estimate for that indication is largely driven by the indication group). The structure of the formula such as nesting hierarchy (e.g., nesting study random effects under sites, or treating study effects and site effects as separate random effects) and nesting depth, which fixed effects are allowed to vary under a given group (e.g., if enrollment duration is allowed to vary under each site) may be determined using the model assessment metrics.

The list of experimental formulae may include several variations of grouping factors and nesting structures. A few different examples of variable grouping, nesting, and depth for the structure are listed below:

(1+EnrollPeriod|SiteID): Under the assumption that enrollment period (EnrollPeriod) can have a varying slope within a site, allowing enrollment rate to vary from site-to-site;

(1|Country/SiteID): Assuming a certain country-level enrollment effect, sites can be nested under countries and both can be included as random effects, so the model can regress to the country-level mean when historical data for a single site are not sufficient;

(1|TherapeuticArea/IndicationGroup/Indication): Since study indications can be nested under indication groups and therapeutic areas, the model can regress to higher-level group mean when historical data for a single indication are not sufficient;

(1|IndicationGroup/SiteID): Assuming site performance varies from one indication group to another, nesting sites under indication groups as a random effect can account for such a sub grouping;

(1|Sponsor/IndicationGroup): When sponsors have several different studies under one indication group, within-sponsor variation can be accounted for in an indication group using this nesting structure;

(1+PrevEnrlDuration|SiteID): Historical recent enrollment duration can have a varying slope within a site such that its impact on recent enrollment varies from site to site.

The examples above illustrate various ways of accounting for available data, depth of data, hierarchy in data, relationships within the data elements and domain expert opinions. One or more of the effects may be additively combined in the model structure as well. For example, (1+EnrollPeriod|SiteID)+(1|IndicationGroup/SiteID) allows the system to test if EnrollPeriod varies under each site, and if site performance varies under each IndicationGroup. The final choice of the model formula may be determined based on what formula optimizes the assessment metric under the constraints of available data, known constraints about the data structure and depth, and business requirement/use case. Examples of known constraints are that IndicationGroup cannot be nested under Indication and Country cannot be nested under a SiteID or Sponsor. An example of a business requirement/use case is if the model is to be used at the onset of a study, data collected as part of the study to build the model and subsequently make predictions cannot be used.

As another aspect of the present invention, the predicted enrollment may be revised during the study based on data generated in the study. For example, informative factors used to revise and update predictions may include the change of principal investigator for a given study-site, time taken by sites to query data in the study, time taken by the first site to enroll the first patient, etc.

To assess the models, metrics such as mean absolute error (MAE: lower is better) and Pearson correlation (COR: higher is better) may be used. The assessment may be performed at the study level (predicted vs. observed subject count at the end of study from all sites) and the study-site level (predicted vs. observed subject count at the end of study from individual sites). Each model was assessed separately (blocks 224 and 234) before combining the model outputs in block 299 to assess the aggregated model performance in block 240. As discussed several paragraphs earlier, variations of model formulae and covariate combinations were tried until the lowest possible MAE and/or the highest correlation possible was achieved at the study level.

There was no specific baseline model available for comparison and assessment of model performance, so a conditional modeling approach was used to define the baseline model. This approach essentially uses the historical enrollment data available for a given site (controlling for indication group) and the site activation schedule to predict site-level and study-level enrollment. For example, for a breast cancer study conducted in January 2012 by a given sponsor, using a set of sites, the historical performance of those selected sites for prior (to January 2012) breast cancer studies were used to estimate their enrollment rate and make forecasts. If a site did not have any prior breast cancer studies, the next level in the study metrics hierarchy was used (therapeutic area in this example), and the enrollment rate for the site-based estimate on its performance in that group was estimated.

Table 1 is a performance summary for each individual model:

TABLE 1

| Study-site Total Enrollment Count | | | Study-site Total Enrollment Count | | |
|---|---|---|---|---|---|
| | Scaled MAE | COR | | Scaled MAE | COR |
| TTFE Model | 0.96 | 0.35 | FELE Model | 1.53 | 0.45 |
| Baseline | 1.14 | 0.21 | Baseline | 2.25 | 0.26 |
| Study Total Enrollment Count | | | Study Total Enrollment Count | | |
| | Scaled MAE | COR | | Scaled MAE | COR |
| TTFE Model | 0.62 | 0.38 | FELE Model | 0.97 | 0.78 |
| Baseline | 0.73 | 0.32 | Baseline | 1.05 | 0.66 |

For the chosen model formula and covariates, both models (TTFE and FELE) provided a lower MAE and a higher COR over the baseline models for both the study level and study-site level predictions.

FIGS. 6A and 6B show the results of embodiments of the invention. FIG. 6A shows site-level predictions for 172 unique sites generated for one particular study. The dotted, dashed, and solid lines represent predicted enrollment curves for different sites in the study. (The curves can be overlapping or close, so it is difficult to visually differentiate each individual line.) FIG. 6B shows a study-level cumulative subject estimate from the 172 unique sites in FIG. 6A. The long-and-short dashed line shows the mean estimate, and the short dashed lines show the 95% confidence bound.

Figure 7A:
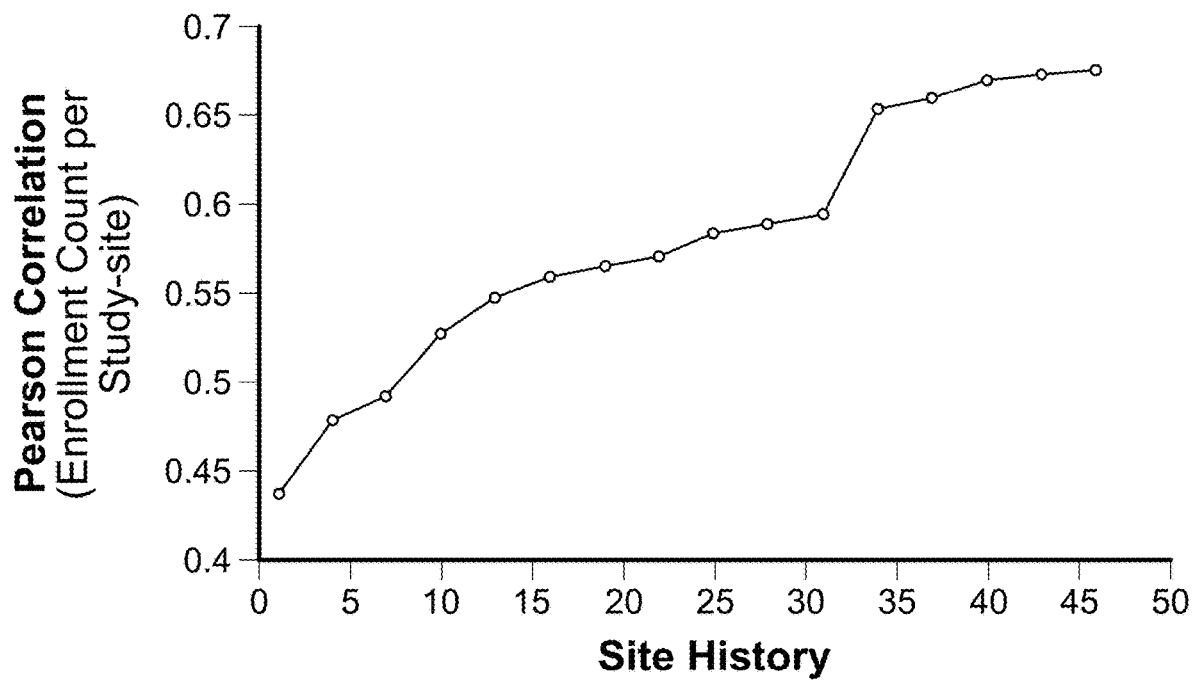
FIGS. 7A and 7B are graphs showing correlation and the mean absolute error, respectively, as a function of trial history for a site, according to an embodiment of the present invention.
Figure 7B:
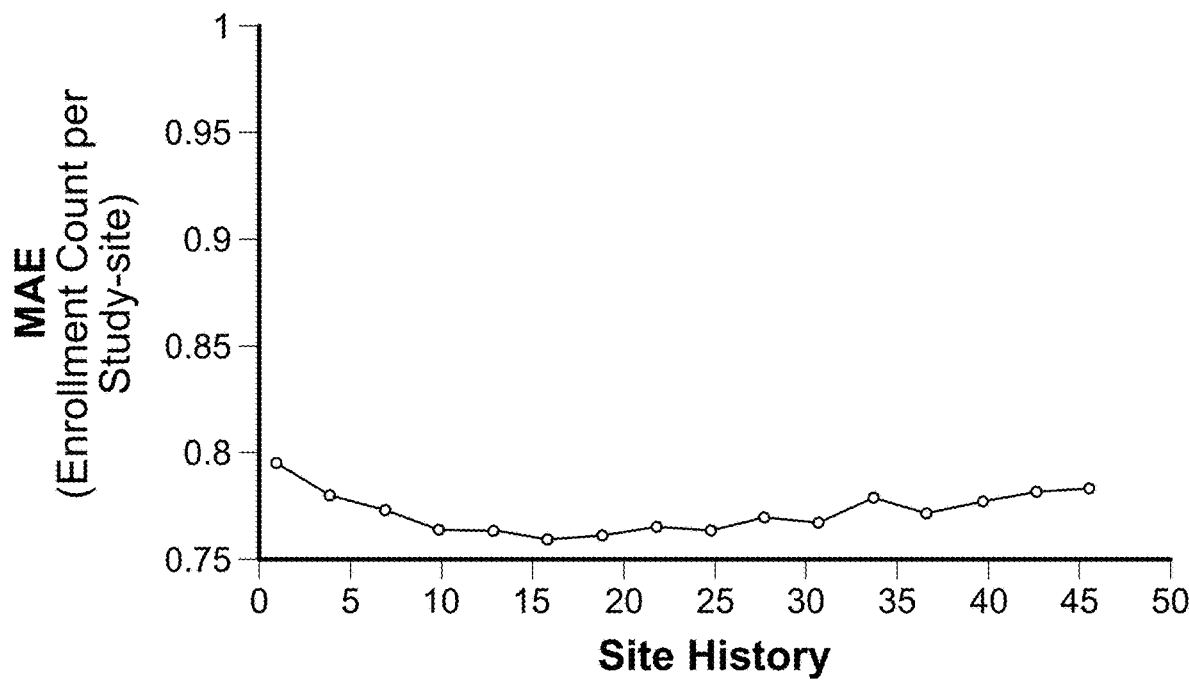

Accordingly, a system and method for predicting clinical trial enrollment are provided that beneficially provide researchers and sponsors an improved measure of subject enrollment for planning purposes as compared to using historical enrollment rate alone. The aspects that differentiate this approach and help overcome some of the limitations of prior methods include:

Using a machine-learning approach to create a standardized site master managed database. FIGS. 7A and 7B show the benefit of having a deep site history: FIG. 7A shows improved correlation while FIG. 7B shows that the error is maintained as sites had more history (the x-axis shows the number of studies associated with a site ID).

The use of mixed effects models to account for study-to-study and site-to-site variation.

The use of enrollment duration as a predictor that allows enrollment rate to change for a given site as the study progresses.

The use of a Bayesian modeling paradigm to facilitate handling large datasets.

Aspects of the present invention may be embodied in the form of a system, a computer program product, or a method. Similarly, aspects of the present invention may be embodied as hardware, software or a combination of both. Aspects of the present invention may be embodied as a computer program product saved on one or more computer-readable media in the form of computer-readable program code embodied thereon.

The computer-readable medium may be a computer-readable storage medium or a computer-readable signal medium. A computer-readable storage medium may be, for example, an electronic, optical, magnetic, electromagnetic, infrared, or semiconductor system, apparatus, or device, or any combination thereof.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that may communicate, propagate, or transport a program for use by or in connection with an instruction execution system, apparatus, or device.

Computer program code in embodiments of the present invention may be written in any suitable programming language. The program code may execute on a single computer, or on a plurality of computers. The computer may include a processing unit in communication with a computer-usable medium, where the computer-usable medium contains a set of instructions, and where the processing unit is designed to carry out the set of instructions.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A method for predicting subject enrollment for a clinical study, comprising:
   generating a database of unique healthcare sites, the database including data regarding site enrollment history for at least some of the sites and having no duplicated sites;
   splitting the database of unique healthcare sites into training data and testing data;
   creating a first training set from the training data based on time to site activation;
   creating a second training set from the training data based on enrollment count from the time of site activation to the time of last subject enrollment;
   training a first statistical model using the first training set to predict a time to site activation for each site in the unique healthcare site database;
   training a second statistical model using the second training set to predict enrollment count for periods of time after the time of site activation for each site in the unique healthcare site database;
   generating a clinical study enrollment model for predicting subject enrollment by:
      using the predicted time to site activation produced by the first statistical model for each site as an input for generating the predicted enrollment count for the periods of time after the time of site activation for each site using the second statistical model, and
      aggregating the predicted enrollment count for each period of time for each site to predict cumulative enrollment for the clinical study for each period of time;
   using the clinical study enrollment model to generate an initial prediction of subject enrollment for each site in the unique healthcare database;

receiving updated site enrollment history;
using the clinical study enrollment model to generate a revised prediction of subject enrollment for each site in the unique healthcare database, wherein the revised prediction improves as site enrollment history increases; and
using at least one of the initial prediction or the revised prediction for each site to improve the execution of the clinical study;
wherein:
the first statistical model is a hierarchical model for the time to site activation in the training data; and
the second statistical model is a hierarchical model for the enrollment count from the time of site activation to the time of last subject enrollment in the training data.

2. The method of claim 1, wherein generating a database of unique healthcare sites comprises:
receiving a database of entities;
determining which of the entities is related to healthcare;
applying a gradient boosting model to pairs of healthcare-related entities that have a common geographic characteristic;
calculating a matching probability for each pair of healthcare-related entities;
when the matching probability for a pair of healthcare-related entities at least equals a pre-determined threshold, manually reviewing the pair of healthcare-related entities to determine whether they are a single healthcare site;
when the pair of healthcare-related entities is determined to be a single healthcare site, adding the single healthcare site to the database of unique healthcare sites as a new record or as a site alias for an existing record; and
when the matching probability for the pair of healthcare-related entities is less than the pre-determined threshold, adding the pair of healthcare-related entities to the database of unique healthcare sites.

3. The method of claim 2, wherein generating a database of unique healthcare sites further comprises adding sites from a site master managed database to the database of unique healthcare sites, and wherein sites from the site master managed database and the database of unique healthcare sites are compared to eliminate duplicate sites and integrate the data about each site.

4. The method of claim 2, wherein the common geographic characteristic is selected from a group consisting of country, state, and zip code.

5. The method of claim 2, wherein the site master managed database is generated by:
receiving a database of study sites;
preparing the information for the study sites;
applying a gradient boosting model to pairs of study sites and sites from the database of unique healthcare sites that have a common geographic characteristic;
calculating a matching probability for each pair of study sites and sites from the database of unique healthcare sites;
when the matching probability for a pair of study sites and sites from the database of unique healthcare sites at least equals a pre-determined second threshold, manually reviewing the pair of study sites to determine whether they are a single study site; and
when the pair of study sites is determined to be a single study site, adding the single study site to the site master managed database.

6. The method of claim 5, wherein when the matching probability for the pair of study sites is less than the pre-determined second threshold, adding the study sites to the database of unique healthcare sites when the names and addresses for the study sites exist and are recognizable.

7. The method of claim 5, wherein after the information for the study sites is prepared, when a first study site is not matched with any site in the database of unique healthcare sites having a common geographic characteristic, adding the first study site to the database of unique healthcare sites when the name and address for the first study site exists and is recognizable.

8. The method of claim 5, wherein the common geographic characteristic is selected from a group consisting of country, state, and zip code.

9. The method of claim 1, wherein the first statistical model and the second statistical model each converge using maximum likelihood point estimation or Bayesian regression estimation.

10. The method of claim 1, wherein the first statistical model is a generalized linear mixed effects model comprising at least one random effect variable.

11. The method of claim 1, wherein the second statistical model is a generalized linear mixed effects model comprising at least one random effect variable.

* * * * *